United States Patent [19]

Herslöf et al.

[11] Patent Number: 5,354,773
[45] Date of Patent: Oct. 11, 1994

[54] USE OF BAFILOMYCINE AND DERIVATIVES TO TREAT BONE DISEASES

[75] Inventors: Margareta Herslöf, Mölndal; Björn Wallmark, Mölnlycke, both of Sweden; Kalervo Väänänen, Oulu, Finland

[73] Assignee: Aktiebolaget Astra, Sodertalje, Sweden

[21] Appl. No.: 849,020

[22] PCT Filed: Oct. 22, 1990

[86] PCT No.: PCT/SE90/00684

§ 371 Date: Jun. 1, 1992

§ 102(e) Date: Jun. 1, 1992

[87] PCT Pub. No.: WO91/06296

PCT Pub. Date: May 16, 1991

[30] Foreign Application Priority Data

Oct. 24, 1989 [SE] Sweden .................. 8903529-9

[51] Int. Cl.$^5$ .................................. A61K 31/70
[52] U.S. Cl. .................................. 514/450
[58] Field of Search .................................. 514/450

[56] References Cited

U.S. PATENT DOCUMENTS

4,558,139 12/1985 Hagenmaier .................. 549/271

FOREIGN PATENT DOCUMENTS

0120392 3/1984 European Pat. Off. .

OTHER PUBLICATIONS

Kretschmer, A. "The Structures of Novel Insecticidal Macrolides: Bafilomycins D and E, and Oxohygrolidin", Agric. Biol. Chem., 49: 2509–2511, 1985.
Hensens et al. "Structure of the Sodium and Potassium Ion activated Adenosinetriphosphatase Inhibitor L–681,110" J. Am. Chem. Soc. 105: 3672–3679, 1983.
Meyer et al. "Bafilomycin-A$_1$-21-O-(α-L-rhamnopyranosid): Strukturaufklärung durch chemische Verknüpfung mit Bafilomycin A$_1$ und Leucanicidin" Helv. Chem. Acta. 68: 83–94, 1985.
Werner et al. "Metabolic Products of Microorganisms, 224 Bafilomycins, a New Group of macrolide Antibiotics Production, Isolation, Chemical Structure and Biological Activity" J. of Antibiotics 37: 110–117, 1984.
Wilton et al. "PD 118, 576: A New Antitumor Macrolide Antibiotic" J. of Antibiotics 38: 1149–1452, 1985.
Seto et al. "The Isolation and Structures of Hygrolidin Amide and Defumarylhygrolidin" J. Antibiotics 37: 610–613, 1984.
Geotz et al. "A new Antiparasitic Macrolide Fermentation, Isolation and Structure" J. Antibiotics 38: 161–168, 1985.
Corey et al. "Stereochemistry of the Hygrolidins" Tetrah. Let. 25: 4325–4325, 1984.
Kretschmer et al. "the Structure of Nover Insecticidal Macrolides: Bafilomycins D and E, and Oxohygrolidin–. . . " Agric. Biol. Chem. 49: 2509, 1985.
Reynolds, J. J. "Organ cultures of bone: Studies on the physiology and pathology of resorption". In: Organ culture in biomedical research, Bulls M., and Monnichendam eds. Cambridge University Press, pp. 355–366, 1976.

*Primary Examiner*—Marianne M. Cintins
*Assistant Examiner*—T. J. Criares
*Attorney, Agent, or Firm*—White & Case

[57] ABSTRACT

A method for the treatment of diseases related to loss of bone mass such as osteoporosis, Paget's disease of bone, hyperparathyroidism, parodontal diseases and implant-related bone loss comprising administration to a patient suffering therefrom an amount of a compound of formula (I), or a pharmaceutically acceptable salt thereof, effective to mitigate the symptoms of the bone disease.

11 Claims, No Drawings

USE OF BAFILOMYCINE AND DERIVATIVES TO TREAT BONE DISEASES

FIELD OF THE INVENTION

The present invention is related to a novel method for the treatment of several bone affecting diseases, especially osteoporosis, which are characterized by loss of bone mass.

BACKGROUND OF THE INVENTION

The balance in normal subjects between on the one hand bone formation, which is associated with the number and activity of osteoblasts, that is cells associated with the production of bone in the organism, and on the other hand bone loss, which is associated with the number and activity of osteoclasts, that is cells associated with the absorption and removal of bone, is disturbed in several bone affecting diseases. At the present time there is no good treatment for any of these diseases, among which can be mentioned osteoporosis, Paget's disease of bone, hyperparathyroidism and related disorders, and several malignant neoplasms where tumor cells are producing osteoclast-activating factors and cause hypercalcemia.

Worldwide the most urgent need is for the treatment of osteoporosis and tumor associated hypercalcemia. In some areas, e.g. in England and in some other parts of Europe there is also high incidence of Paget's disease of bone.

In osteoporosis bone formation as well as bone resorption are disturbed, resulting in decreased bone mass. Osteoporosis predominantly affects the elderly, but also other groups such as postmenopausal women, where an estrogen deficit is believed to be a significant etiological factor, and immobilized patients. At this point it is not possible to clear up the whole picture of the disease mechanism and estimate which is the primary cause of osteoporosis. However, about 25% of osteoporotic females belong to what is called "rapid bone losers" and at least in those patients the bone resorption rate is probably increased. Landry and Fleisch showed in immobilization induced osteoporosis that bone resorption rate was accelerated, (Landry, M. and Fleisch, H,: The influence of immobilization on bone formation as evaluated the incorporation of tetracyclines. J. Bone Joint Surg. 46B: 764, 1964).

The clinical manifestations of osteoporosis comprise fractures, especially hip fractures, but also vertebral fractures and fractures of the proximal radius, and complication of such fractures.

In Finland it has been estimated that about 10% of all surgical hospital beds are used for the treatment of osteoporosis related fractures (Lüthje, P.: Reisiluunkaulan ja trokantterin murtumapotilaiden hoito ja ennuste sekä hiodon kustannukset. Thesis. Helsinki 1983).

The present methods for the treatment of osteoporosis include exercise; administration of estrogen, especially for postmenopausal women; and consumption of calcium or calcium containing material such as milk. Calcitonin, a hormone associated with calcium metabolism, has also been used in the treatment of osteoporosis. None of these methods of treating osteoporosis results in increase of the bone mass.

Several malignant tumors are known to be associated by hypercalcemia which is due to increased osteoclastic activity. This is a common complication for instance in the case of breast cancer and prostate cancer which are both one of the most common malignant tumors. Hypercalcemia is due to both systemic and local factors. Some malignant cells are known to secrete agents which stimulate bone resorption (Sato, K., Fujii, Y. Kachivehi, T., Kasono, K., Shizume, K.: Production of interleukin 1 alpha (IL-1α)-like activity and colony stimulating activity by clonal squamous cell carcinomas derived from patients with hypercalcemia and leucocytosis. In: Calcium Regulation and Bone Metabolism Vol. 9 (eds. D. V. Cohu, T. J. Martin, P. J. Meunier), 1986).

In malignant hypercalcemia calcitonin and diphosphonate treatment has been used.

Paget's disease (or osteitis deformans) of bone is a disease of unknown etiology where bone resorption and remodelling are increased leading sometimes even to the fractures of affected bone. Bone pain is the main indication of treatment in these patients. In these patients there is highly elevated local osteoclastic bone destruction. The incidence of osteoitis deformans is very low in Scandinavian countries. In England it has been estimated to be present in 3–4% of population on the basis of autopsy studies (Anderson's Textbook of Pathology 1986). It is very rare in patients under 40 years. Calcitonin and diphosphonates are also used in the treatment of Paget's disease.

Other disease states for the treatment of which antagonists to osteoclastic activity might be useful, are periodontal diseases and prosthetic and implant bone losses.

It is an object of the present invention to provide compounds which by affecting the balance between osteoblast and osteoclast activity can be useful for the prophylactic and therapeutic treatment of diseases as indicated above which are associated with bone loss. It is believed that the use of these compounds will also ultimately result in an increase of the bone mass.

PRIOR ART

Bafilomycins and related 16-membered diene macrolides are known in the art, e.g. EP-A2-0120392, G. Werner et. al., J. Antibiotics 1984, 37, 110, A. Kretschmer et. al., Agric. Biol. Chem. 1985, 49, 2509, O. D. Hensens et. al., J. Amer. Chem. Soc., 1983, 105, 3672, E. J. Corey et. al., Tetr. Lett. 1984, 25, 4325, M. Meyer et. al., Helv. Chim. Acta 1985, 68, 83, M. A. Goetz et. al., J. Antibiotics 1985, 38, 161, J. H. Wilton et. al., J. Antibiotics 1985, 38, 1449, H. Seto et. al., J. Antibiotics 1984, 37, 610.

Outline of the present invention

According to the present invention it has been found that compunds of the general formula I, which are known as Bafilomycin compounds, Hygrolidin compounds, and related compounds, as well as pharmaceutically acceptable salts thereof are effective as inhibitors of basal and stimulated bone resorption and are useful as medicals for the treatment of diseases related to bone loss and increased bone resorption, such as osteoporosis, Paget's disease of bone, hyperparathyroidism, both primary and secondary, malignant neoplasms where tumor cells are producing osteoclast-activating factors and cause hypercalcemia, immobilization-induced osteroporosis, periodontal diseases and prostetic and implant-related bone losses.

The compounds of the invention are of the following formula I, and pharmaceutically acceptable salts thereof:

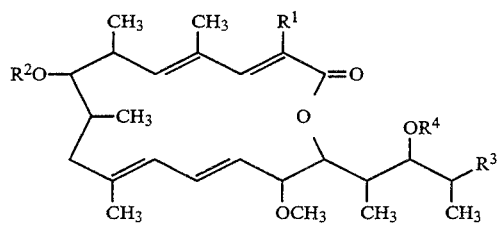

wherein

1. $R^1$ = OMe   $R^2$ = H   $R^4$ = H,

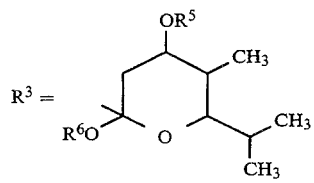

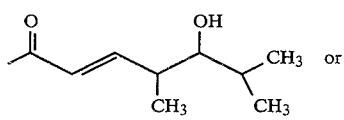

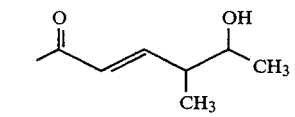

$R^5$ = H,  MeCO,  HOOCCHCHCO,

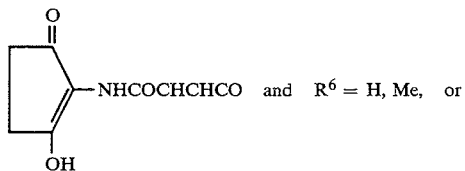  and   $R^6$ = H, Me, or

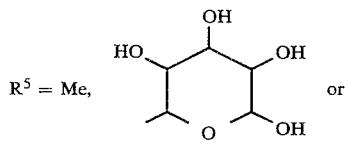

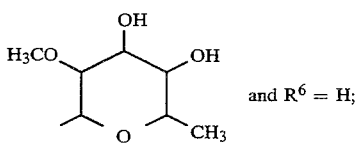

2. $R^1$ = OMe   $R^2$ = MeCO   $R^4$ = H

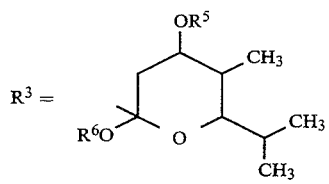

$R^5$ = MeCO   $R^6$ = H, Me

3. $R^1$ = Me   $R^2$ = H   $R^4$ = H

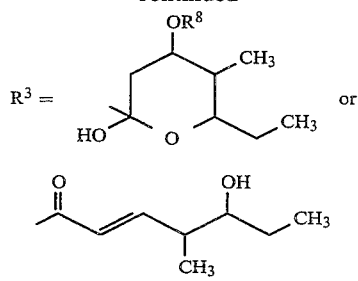

-continued

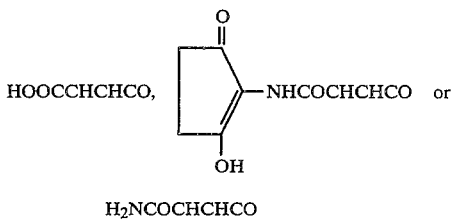

$R^8$ = H,  HOOCCHCHCO,  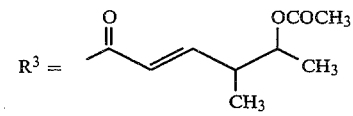 or $H_2NCOCHCHCO$

4. $R^1$ = OMe   $R^2$ = MeCO   $R^4$ = MeCO   and

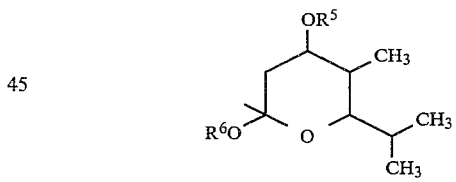

"Me" in the formulas designates methyl. The formula I specifically indicates those stereoisomers which are described in the literature referred to above. Thus, the formula I includes the following compounds: Bafilomycin $A_1$, $A_2$, $B_1$, $B_2$, $C_1$, $C_2$, and D (according to the nomenclature used by Werner et al (1984); see above) as well as Hygrolidin, Hygrolidin amide, Defumarylhygrolidin and Oxohygrolidin (according to the nomenclature used by Seto et al. (1984) and Kretschmer et al. (1985); se above).

Preferred compounds of the invention are those of formula I, wherein $R^1$ is OMe, $R^2$ and $R^4$ are H, $R^3$ is

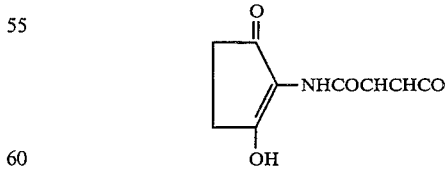

and $R^5$ and $R^6$ are as described above. Further preferred of these compounds are those wherein $R^5$ is H, HOOCCHCHCO or

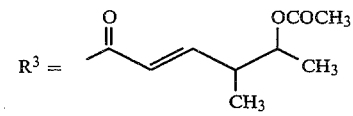

and $R^6$ is as described above. Still further preferred of these compounds are those wherein $R^5$ is H or HOOCCHCHCO and $R^6$ is as described above. Particularly preferred of these compounds are the compound wherein $R^5$ and $R^6$ are both H (Bafilomycin $A_1$) and the compound wherein $R^5$ is HOOCCHCHCO and $R^6$ is H (Bafilomycin $C_1$).

Accordingly, the invention relates to a method for the prophylactic and therapeutic treatment of each of the ailments above by administering to a host in need thereof of an effective amount of a compound of the formula I optionally together with a pharmaceutically acceptable carrier a pharmaceutical preparation for use in the prophylactic and therapeutic treatment of each of the ailments above comprising a compound of the formula I as active ingredient the use of a compound of the formula I in the manufacture of a medicament for the prophylactic and therapeutic treatment of each of the ailments above a method for improving the healing rate of bone fractures by administering to a host in need thereof of an effective amount of a compound of the formula I Pharmacological tests In order to evaluate the inhibitory effect on bone resorption, an in vitro model, the mouse calvaria explant model (described in Reynolds, J. J. Organ cultures of bone: Studies on the physiology and pathology of bone resorption. In: Organ culture in biomedical research (Bulls M., and Monnichendam M. A. eds) Cambridge University Press, p.p. 355–366, 1976) was used. In this model the effects of the compounds on the basal and the parathyroidhormone (PTH)-induced bone resoprtion are measured.

RESULTS

The compound of structure I where $R^1=$OMe, $R^2=$H, $R^4=$H, $R^3=$

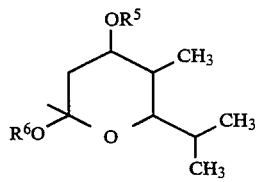

$R^5=$H and $R^6=$H, bafilomycin A$_1$, was tested. As can be seen from Table 1 the compound significantly inhibits PTH-induced bone resorption.

TABLE 1

| Effect of Bafilomycin A$_1$ on parathyroid hormone induced bone resorption in vitro | |
|---|---|
| | % Release of $^{45}$Ca$^{2+}$ |
| Control (=basal) | 5.4 ± 0.35 |
| PTH | 30 ± 4.3 |
| PTH + $10^{-10}$ mol/l Bafilomycin A$_1$ | 27 ± 5.0 |
| PTH + $10^{-9}$ mol/l Bafilomycin A$_1$ | 18 ± 2.2 |
| PTH + $10^{-8}$ mol/l Bafilomycin A$_1$ | 6.3 ± 0.41 |
| PTH + $10^{-7}$ mol/l Bafilomycin A$_1$ | 3.5 ± 0.52 |

PTH=Parathyroidhormone. PTH was used at a concentration of $10^{-8}$ mol/l. The results are mean+SEM of 5 half-calvaria in each group. The calvarial bones were cultured with PTH and Bafilomycin A$_1$ for 72 hours. The estimated IC$_{50}$ value (IC$_{50}=$the concentration of drug that gives 50% inhibition of the response) was estimated to $10^{-9}$ mol/l.

Fcr clinical use the compounds of the formula I are formulated into pharmaceutical formulations for oral, rectal, parenteral or other mode of administration. The pharmaceutical formulation contains a compound of the formula I in combination with a pharmaceutically acceptable carrier. The carrier may be in the form of a solid, semi-solid or liquid diluent, or a capsule. These pharmaceutical preparations are a further object of the invention. Usually the amount of active compounds is between 0.1–95% by weight of the preparation, between 0.2–20% by weight in preparations for parenteral use and between 1 and 50% by weight in preparation for oral administration.

The typical daily dose of the active substance varies within a wide range and will depend on various factors such as for example the individual requirement of each patient, oral and of administration and the disease. In general, oral and parenteral dosages will be in the range of 0.1 to 500 mg per day of active substance.

What we claim is:

1. A method for the treatment of osteoporosis by administering to a host in need of such treatment a therapeutically effective amount of a compound of a formula I below, or a pharmaceutically acceptable salt thereof, optionally together with a pharmaceutically acceptable carrier:

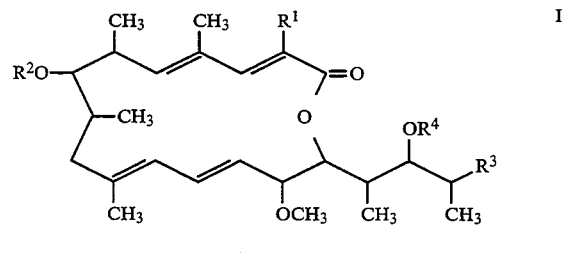

wherein a) $R^1 =$ OMe $R^2 =$ H $R^4 =$ H, $R^3 =$

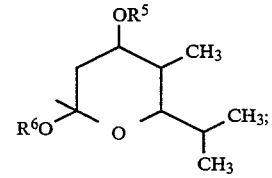

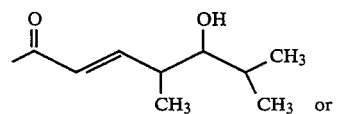

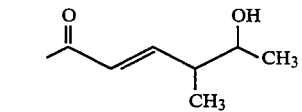

$R^5 =$ H, MeCO, HOOCHCHCO,

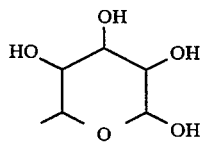

and $R^6 =$ H, Me, or $R^5 =$ Me,

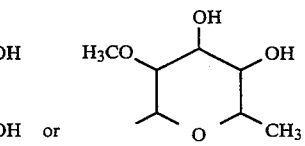

and $R^6 =$ H;

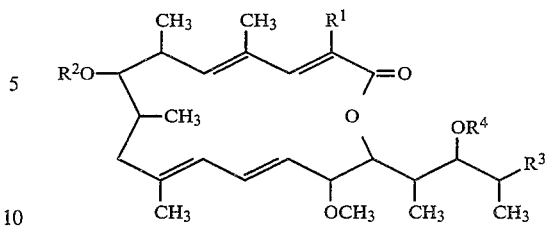

wherein $R^1$ = OMe  $R^2$ = H  $R^4$ = H, $R^3 =$ 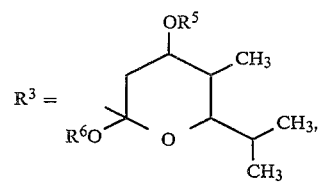

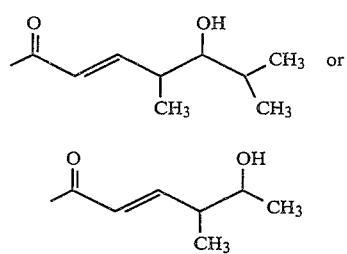

$R^5$ = H, MeCO, HOOCHCHCO,

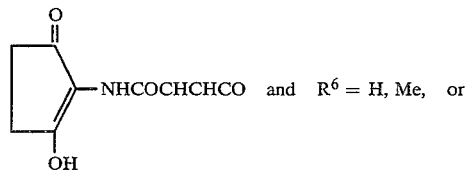 and $R^6$ = H, Me, or $R^5$ = Me, 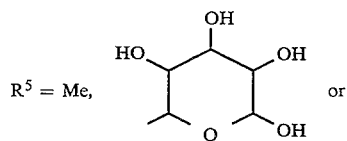 or

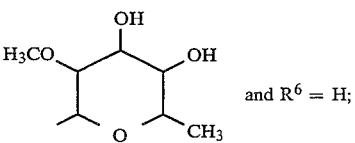 and $R^6$ = H;

$R^1$ = OMe  $R^2$ = MeCO  $R^4$ = H $R^3 =$ 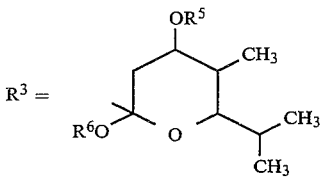

$R^5$ = MeCO  $R^6$ = H, Me;

$R^1$ = Me  $R^2$ = H  $R^4$ = H b) $R^1$ = OMe  $R^2$ = MeCO  $R^4$ = H  $R^3 =$

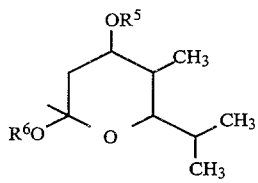

$R^5$ = MeCO  $R^6$ = H, Me;

c) $R^1$ = Me  $R^2$ = H  $R^4$ = H  $R^3 =$

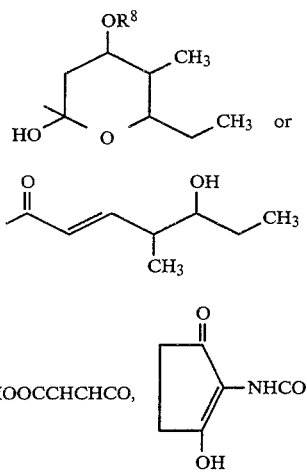

$R^8$ = H, HOOCCHCHCO, 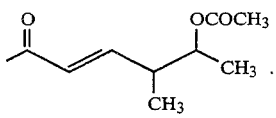

or H$_2$NCOCHCHCO; or d) $R^1$ = OMe  $R^2$ = MeCO  $R^4$ = MeCO and $R^3 =$

2. A method for the treatment of Paget's disease of bone by administering to a host in need of such treatment of a therapeutically effective amount of a compound of the formula I as defined in claim 1, optionally together with a pharmaceutically acceptable carrier.

3. A method for the treatment of primary and secondary hyperparathyroidism by administering to a host in need of such treatment of a therapeutically effective amount of a compound of the formula I as defined in claim 1, optionally together with a pharmaceutically acceptable carrier.

4. A method for the treatment of periodontal diseases, by administering to a host in need of such treatment of a therapeutically effective amount of a compound of the formula I as defined in claim 1, optionally together with a pharmaceutically acceptable carrier.

5. A method for the treatment of prosthetic and implant-related bone loss, by administering to a host in need of such treatment of a therapeutically effective amount of a compound of the formula I as defined in claim 1, optionally together with a pharmaceutically acceptable carrier.

6. A method for the treatment of diseases which exhibit increased bone resorption comprising administering to a host in need of such treatment, an effective amount of a compound of the formula I -continued

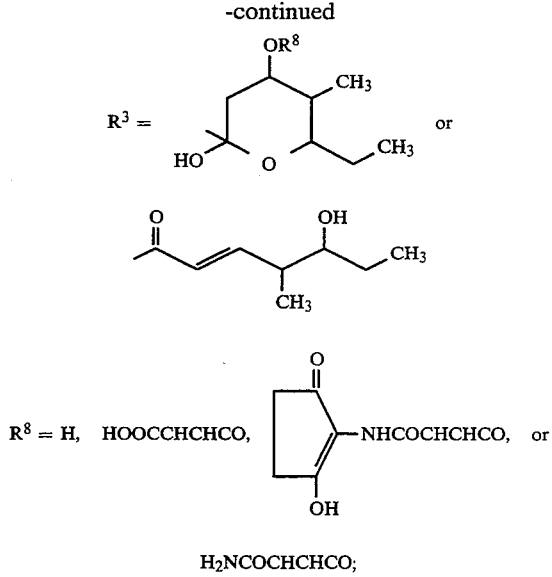

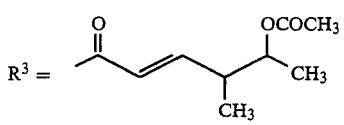

in a pharmaceutically acceptable carrier.

7. A method according to claim 6, wherein the compound of the formula I is Bafilomycin $A_1$.

8. A method according to claim 6, wherein the compound of the formula I is Bafilomycin $C_1$.

9. A method for improving the healing rate of bone fractures by administering to a host in need thereof of an effective amount of a compound as defined in claim 1.

10. A method according to claim 9 wherein the compound of the formula I is Bafilomycin $A_1$.

11. A method according to claim 9 wherein the compound of the formula I is Bafilomycin $C_1$.

* * * * *